US00PP13416P3

(12) United States Plant Patent
Noodelijk

(10) Patent No.: US PP13,416 P3
(45) Date of Patent: Dec. 24, 2002

(54) CHRYSANTHEMUM PLANT NAMED 'RESOMEE'

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 09/757,640

(22) Filed: Jan. 11, 2001

(65) Prior Publication Data

US 2002/0129415 P1 Sep. 12, 2002

(51) Int. Cl.[7] ..... A01H 5/00

(52) U.S. Cl. ..... Plt./291

(58) Field of Search ..... Plt./291

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'RESOMEE' characterized by its large sized blooms with pink ray-florets.

3 Drawing Sheets

BACKGROUND OF THE INVENTION

'RESOMEE' is a product of a breeding-program which had the objective of creating new chrysanthemum cultivars with a decorative type flower, a 8 week response and a medium plant height. The new plant of the present invention comprises a new and distinct cultivar of Chrysanthemum plant. 'RESOMEE' is a seedling from a cross in a breeding program maintained under the control of inventor. The female parent is #93.0202-unpatented-, an unamed seedling not available to inventor for description. The male parent is unknown, being a mixed pollation of a group of male parents. The new and distinct cultivar was discovered and selected as a flowering plant within the progeny of the stated cross by Rob Noodelijk in a controlled environment (greenhouse) in Rijsenhout Holland in September 1998. The first act of asexual reproduction of 'RESOMEE' was accomplished when vegetative cuttings were taken from the initial selection in November 1998 in a controlled environment in Rijsenhout Holland.

SUMMARY OF THE INVENTION

The present invention is a new and distinct variety of chrysanthemum bearing large sized blooms with pink ray-florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
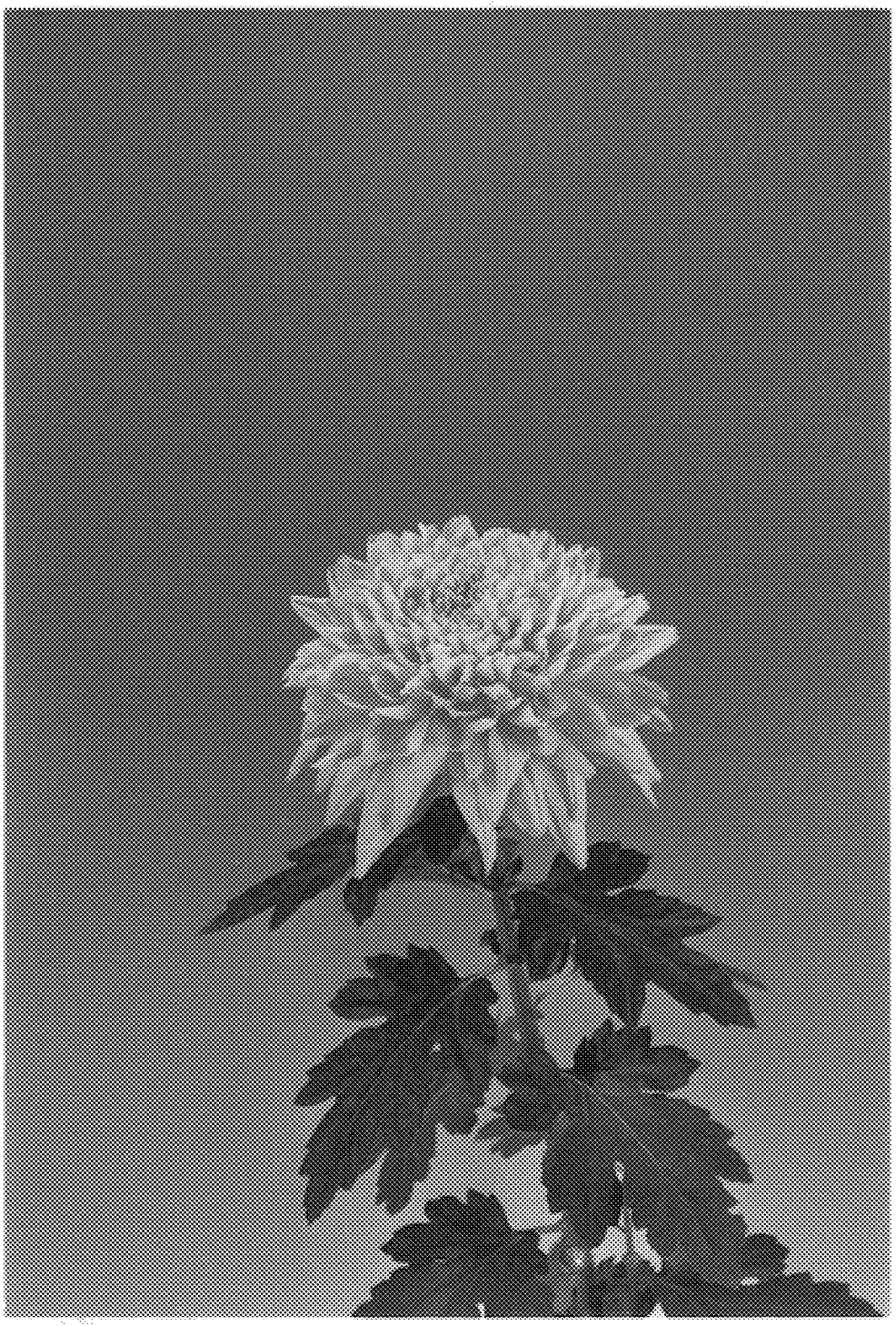
FIG. 1 shows a plant of the cultivar in full bloom.
Figure 2:
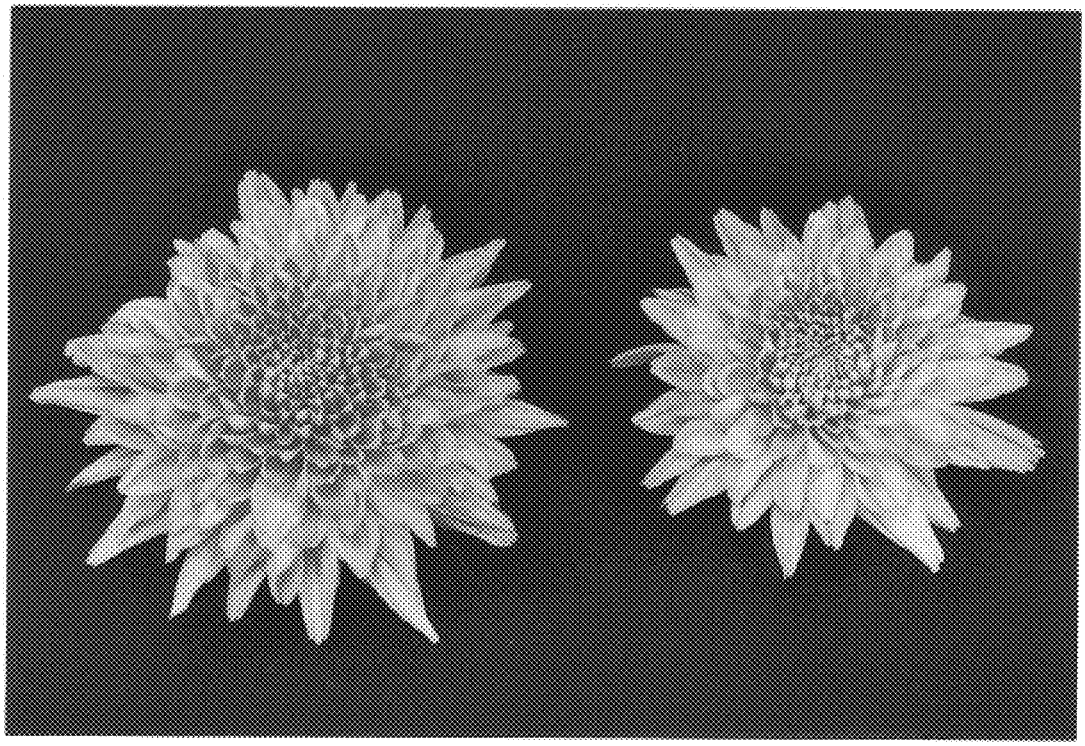
FIG. 2 shows the various stages of bloom of the new cultivar.
Figure 3:
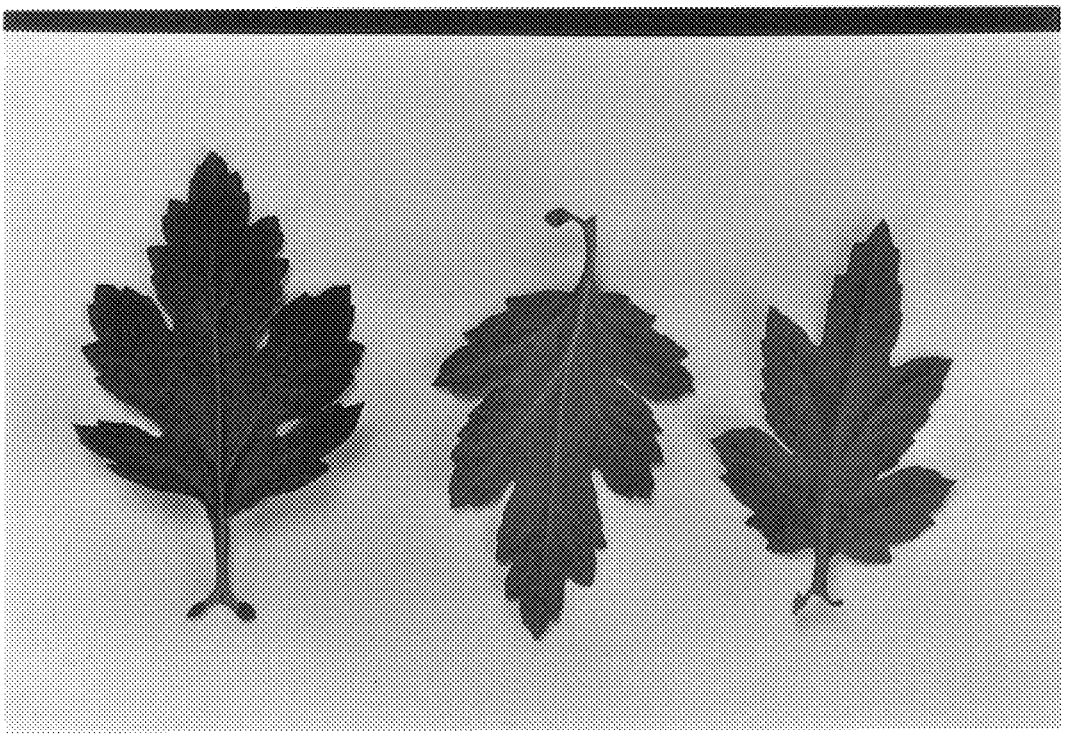
FIG. 3 shows the foliage of the new cultivar.

This new variety of chrysanthemum is of the botanical classification *Chrysanthemum morifolium*. The observations and measurements were gathered from plants grown in April/May in a greenhouse in Rijsenhout Holland in a photo-periodic controlled crop under conditons generally used in commercial practice. The greenhouse temperatures during this crop were at day-time between 18° C. and at night 20° C. After a long day period of 14 days the photo-periodic response time in this crop was 56 days. After the long day period to flowering growth retardants were applied 2 to 3 times in an average dose of 2.5 gram/liter water. The plants were observed (directly) during the flowering of this crop. No tests were done on disease or insect resistance or susceptibility. No tests were done on cold or drought tolerance. This new variety produces large sized blooms with pink ray-florets blooming on the plant for 3 weeks. This new variety of chrysanthemum has been found to retain its distinctive characteristics throughout successive propagations however the phenotype may vary significantly with variations in environment such as light intensity and temperature. To show the phenotype as decribed 'RESOMEE' can be planted without assimilation lightning (high pressure sodium lamps) between week 50 and week 40 of the next year under greenhouse conditions in Holland. With assimilation light (minimum level 2500 lux) it can be planted year round under greenhouse conditions in Holland.

From the cultivars known to inventor the most similar existing cultivar in comparison to 'RESOMEE' is 'ELEONORA'. When 'ELEONORA' and 'RESOMEE' are being compared the following differences and similarities are noticed: The differences of 'ELEONORA' and 'RESOMEE' is the flowerform: 'RESOMEE' has a decorative flower, 'ELEONORA' a anemone type flower.

The following is a description of the plant and characteristics that distinguish 'RESOMEE' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Resomee'

Bud:

*Size.*—Large, cross-section 1.4 cm, height 1.2 cm.
*Color.*—Greyed-purple 186D.
*Involucral bracts.*—2 rows, length 9 mm, width 4 mm.

*Involucral bracts among disc-florets.*—Not present.
*Involucral bracts color.*—Green 138 A.

Bloom:
*Type.*—Single decorative.
*Height.*—Flat high, 6.0 cm.
*Size.*—Large.
*Fully expanded.*—11.0 cm.
*Number of blooms per stem.*—1 (one).
*Performance on the plant.*—3 weeks.
*Seeds if crossed.*—Produced in small quantities oval shaped grey-brown 199 A, 2 mm in length.
*Fragrance.*—Typical chrysanthemum, slight.

Color:
*Center of the flower.*—Immature purple 75 A. Mature purple 75 B.
*Color of upper surface of the ray-florets.*—Purple 75 B.
*Color of the lower surface of the ray-florets.*—Purple 76 D.
*Tonality from distance.*—A disbudded mum with large pink flowers.
*Color of the upper surface of the ray-florets after aging of the plant.*—Purple 76 D.

Ray florets:
*Texture.*—Upper and under side smooth.
*Number.*—180–190.
*Cross-section.*—Flat to concave.
*Longitudinal axis of majority.*—Straight.
*Length of corolla tube.*—Medium, 1.0–1.4 cm.
*Ray-floret margin.*—Entire.
*Ray-floret length.*—5.0–6.0 cm.
*Ray-floret width.*—0.9–1.3 cm.
*Ratio length/width.*—High.
*Shape of tip.*—Pointed.

Reproductive organs:
*Stamen.*—Not present.
*Pollen.*—Not present.
*Styles* (*present in ray florets*).—Thin.
*Style color.*—Yellow-green 144 A.
*Style length.*—3 mm.
*Stigmas.*—Yellow-green 144 A.
*Stigma width.*—1 mm.
*Ovaries.*—Enclosed in calyx.

Plant:
*Form.*—A disbudded mum meant for erect culture.
*Growth habit.*—Upright.
*Growth rate.*—Rapid.
*Height.*—125 cm.
*Internodes.*—2.5–3.0 cm.
*Spray formation.*—Not applicable; disbudded.
*Stem color.*—Green 138 A.
*Stem strength.*—Strong.
*Stem brittleness.*—Absent.
*Stem anthocyanin coloration.*—Absent.
*Peduncle length.*—4.0 cm.
*Peduncle color.*—Green 138 A.
*Peduncle, angle with stem.*—40°.
*Flowering response*(*photo-periodic controlled crop, not natural season*).—56 days.

Foliage:
*Color mature.*—Upper side green 139 A. Under side green 137 A.
*Color immature.*—Upper side green 139 A. Under side green 137 A.
*Size.*—Large; length 9.5 cm, width 8.0 cm.
*Quantity* (*number per single stem*).—32–35.
*Shape.*—Round.
*Texture upper side.*—Fleshy and glabrous.
*Texture under side.*—Pubescent.
*Venation arrangement.*—Palmate.
*Shape of the margin.*—Crenated.
*Shape of base of sinus between lateral lobes.*—Acute.
*Margin of sinus between lateral lobes.*—Diverging.
*Shape of base.*—Truncate.
*Apex.*—Cuspidate.
*Petiole color.*—Green 138A.

Differences with the comparison Varieties

| | 'ELEONORA' | 'RESOMEE' |
|---|---|---|
| Flower form | Anemone type | Decorative |

I claim:

1. A new and distinct variety of chrysanthemum plant as described and illustrated.

* * * * *